(12) United States Patent
Kannan et al.

(10) Patent No.: US 8,729,171 B2
(45) Date of Patent: May 20, 2014

(54) SUPERCRITICAL CARBON-DIOXIDE PROCESSED BIODEGRADABLE POLYMER NANOCOMPOSITES

(75) Inventors: Rangaramanujam M. Kannan, Novi, MI (US); Kevin C. Baker, Royal Oak, MI (US); Robert Bellair, Warren, MI (US); Mihai Manitiu, MaComb, MI (US); Harry Herkowitz, West Bloomfield, MI (US)

(73) Assignees: Wayne State University, Detroit, MI (US); William Beaumont Hospital, Royal Oak, MI (US)

(*) Notice: Subject to any disclaimer, the term of this patent is extended or adjusted under 35 U.S.C. 154(b) by 3 days.

(21) Appl. No.: 13/010,513

(22) Filed: Jan. 20, 2011

(65) Prior Publication Data

US 2011/0288651 A1 Nov. 24, 2011

Related U.S. Application Data (60) Provisional application No. 61/297,512, filed on Jan. 22, 2010.

(51) Int. Cl.
*C08K 3/34* (2006.01)

(52) U.S. Cl.
USPC ............ 524/445; 428/339; 428/480; 428/500

(58) Field of Classification Search
USPC ..................... 524/445; 428/339, 480, 500
See application file for complete search history.

(56) References Cited

U.S. PATENT DOCUMENTS

| | | | |
|---|---|---|---|
| 6,753,360 B2 | 6/2004 | Mielewski et al. | |
| 6,759,446 B2 | 7/2004 | Lee et al. | |
| 6,767,951 B2 | 7/2004 | Nair et al. | |
| 6,767,952 B2 | 7/2004 | Dontula et al. | |
| 6,811,599 B2 | 11/2004 | Fischer et al. | |
| 7,026,365 B2 | 4/2006 | Lee et al. | |
| 7,084,192 B2 | 8/2006 | Ouchi et al. | |
| 7,129,287 B1 | 10/2006 | Lee et al. | |
| 7,387,749 B2 | 6/2008 | Gulari et al. | |
| 7,501,039 B2 | 3/2009 | Lee et al. | |
| 7,619,025 B2 | 11/2009 | Mohanty et al. | |
| 2003/0180344 A1* | 9/2003 | Wise et al. | 424/423 |
| 2004/0054051 A1* | 3/2004 | Ouchi et al. | 524/314 |
| 2005/0131126 A1* | 6/2005 | Yang et al. | 524/445 |
| 2006/0147538 A1* | 7/2006 | Craig et al. | 424/489 |
| 2007/0032631 A1 | 2/2007 | Ouchi et al. | |
| 2008/0038710 A1 | 2/2008 | Lee et al. | |
| 2008/0177374 A1 | 7/2008 | Zheng et al. | |

OTHER PUBLICATIONS

Mathieu, L.M.; Montjovent, M.O.; Bourban, P.E.; Pioletti, D.P.; Manson, J.A.E.; Journal of Biomedical Materials Research Part A, 2005, vol. 75A, Issue 1, p. 89-97.*
Zeng, C.; Han, X.; Lee, J.; Koelling, K.W.; Tomasko, D.L.; Advanced Materials, 2003, vol. 15, Issue 20, p. 1743-1747.*
Arribas-Garcia I et al.; "Fracture of the anterior iliac crest following monocortical bone graft harvest in bisphosphonate-related mandibular pathological fracture: a case report"; *Oral Surg Oral Med Oral Pathol Oral Radiol Endod*, 107(6): e12-14, 2009.
Baker KC, Bellair RJ, Manitiu M, Herkowitz HN, Kannan RM, "Structure and mechanical properties of supercritical carbon dioxide processed porous resorbable polymer constructs"; *J Mech Behav Biomed Mater.*, 2(6): 620-626, 2009.
Chau AM et al.; "Bone graft substitutes in anterior cervical discectomy and fusion"; *Eur Spine J.*, 18(4): 449-464, 2009.
Georgiou, G et al.; "Polylactic Acid-Phosphate Glass Composite Foams as Scaffolds for Bone Tissue Engineering"; *J. Biomed Mater Res Part B: Appl Biomater.* 80B: 322-331, 2007.
Gualandi C et al.; "Scaffold for tissue engineering fabricated by non-isothermal supercritical carbon dioxide foaming of a highly crystalline polyester"; *Acta Biomater*, 6(1): 130-136, 2010.
Horsch, S et al.; "Supercritical $CO_2$ dispersion of nano-clays and clay/polymer nanocomposites"; *Polymer*, 47:7485-7496, 2006.
Hu Y, et al.; "Fabrication of poly($\alpha$-hydroxy acid) foam scaffolds using multiple solvent systems"; *J Biomed Mater Res.* 59: 563-572, 2001.
Khan Y et al.; "Tissue Engineering of Bone: Material and Matrix Considerations"; *J Bone Joint Surg Am*, 9-: 36-42, 2008.
Kim SS et al.; "A poly(lactide-co-glycolide)/hydroxyapatite composite scaffold with enhanced osteoconductivity"; *J Biomed Mater Res A*, 80(1): 206-215, 2007.
Liu, Lillian; "Bioplastics in Food Packaging: Innovative Technologies for Biodegradable Packaging"; San Jose State University, Feb. 2006; http://www.iopp.org/files/public/SanJoseLiuCompetitionFeb06.pdf; last visited Mar. 11, 2011.
Manitiu M et al.; "Supercritical Carbon Dioxide-Processed Dispersed Polystyrene-Clay Nanocomposites"; *Macromolecules*, 41(21): 8038-8046, 2008.
Mathieu, L.M. et al.; "Bioresorbable composites prepared by supercritical fluid foaming"; *J. Biomed Mater Res.*, 75A:89-97, 2005.
Moroni A et al.; "Can We Improve Fixation and Outcomes? Use of Bone Substitutes"; *J Orthop Trauma*, 23(6): 422-425, 2009.
Nam YS et al.; "Porous biodegradable polymeric scaffolds prepared by thermally induced phase separation"; *J Biomed Mat Res*, 47: 8-17, 1999.
Pavlidou S et al.; "A review on polymer-layered silicate nanocomposites"; *Prog Poly Sci*, 33: 1119-1198, 2008.
Ray, SS et al.; "Polymer/layered silicate nanocomposites: a review from prepareation to processing"; Prog. Polym. Sci. 28; 2003; pp. 1539-1641.
Rezwan K et al.; :Biodegradable and bioactive porous polymer/inorganic composite scaffolds for bone tissue engineering; *Biomaterials*, 27(18): 3413-3431, 2006.
Samartzis D et al.; "Comparison of allograft to autograft in multilevel anterior cervical discectomy and fusion with rigid plate fixation"; *Spine J.*; 3(6): 451-459; 2003.
Sidhu, K.S. et al.; "Anterior cervical interbody fusion with rhBMP-2 and tantalum in a goat model"; Spine Journal, vol. 1 (5); pp. 331-340; 2001.

(Continued)

*Primary Examiner* — Robert Jones, Jr.
(74) *Attorney, Agent, or Firm* — Brinks Gilson & Lione (57) ABSTRACT

A biodegradable nanocomposite and a method of forming a biodegradable nanocomposite are provided. In one aspect, the biodegradable nanocomposite includes a biodegradable polymer and a reinforcing agent substantially dispersed throughout the biodegradable polymer by rapid depressurization of a supercritical fluid. The biodegradable nanocomposite further includes a plurality of pores formed in the nanocomposite, the plurality of pores having an average pore size greater than about 100 μm.

19 Claims, 6 Drawing Sheets

(56) References Cited

OTHER PUBLICATIONS

Teng X, et al.; "Preparation and Characterization of Porous PDLLA/HA Composite Foams by Supercritical Carbon Dioxide Technology"; *J Biomed Mater Res B: Applied Biomaterials*, 81B: 185-193, 2007.

Wang Y, et al.; "Synthesis and Characterization of Collagen-Chitosan-Hydroxyapatite Artificial Bone Matrix"; *J Biomed Mater Res A*, 86(1): 244-252, 2008.

Whittenberg, R.H. et al.; "Compressive strength of autologous and allogenous bone grafts for thoracolumbar and cervical spine fusion"; Spine, vol. 15(10); pp. 1073-1078; 1990.

Wigfield C.C. et al.; "Nonautologous Interbody Fusion Materials in Cervical Spine Surgery"; *Spine*, 26:6:687-694, 2001.

Wigfield, CC et al.; "The New Frenchay Artificial Cervical Joint: Results from a Two-Year Pilot Study"; SPINE; vol. 27, No. 22; pp. 2446-2452; 2002.

Wolfinbarger, L. et al.; "A comprehensive study of physical parameters biomechanical properties and statistical correlations of iliac crest bone wedges used in spinal fusion surgery"; SPINE; vol. 19, Issue 3; pp. 284-295; 1994.

Zeng C, et al.; "Polymer-Clay Nanocomposite Foams Prepared Using Carbon Dioxide"; *Advanced Materials*, 15(20): 1743-1747, Oct. 16, 2003.

\* cited by examiner

Figure 1

Figure 2 comparing human iliac crest (left) to structural bone graft nanocomposite substitute (right).

Figure 3a 100PDLA-35°C         Figure 3b 100PLDA-93A-2.5-35°C

Figure 3c 100PDLA-93A-2.5-100°C

Figure 4. Representative SEM images of fracture surfaces from 100PDLA, 100PDLA-93A-2.5(right)

Figure 5. SAXD data for Cloisite 93A and 100PDLA-93A-2.5 construct.

Figure 6. Rheological data for 100PDLA and 100PDLA-93A-2.5 constructs.

Figure 7. Graph of compressive strength of pure and nanocomposite constructs.

Figure 8. Alkaline phosphatase activity of MC3t3-E1 osteoblasts

SUPERCRITICAL CARBON-DIOXIDE PROCESSED BIODEGRADABLE POLYMER NANOCOMPOSITES

RELATED APPLICATIONS

The present application claims the benefit of the filing date under 35 U.S.C. §119(e) of Provisional U.S. Patent Application Ser. No. 61/297,512, filed Jan. 22, 2010, which is hereby incorporated by reference.

TECHNICAL FIELD

This invention relates to biodegradable polymer nanocomposites and methods of making biodegradable polymer nanocomposites and, in particular to biodegradable polymer nanocomposites suitable for implantable constructs.

BACKGROUND

Increasingly, biodegradable polymers are being used to replace plastic materials formed from petroleum-based products. Biodegradable polymers are used in many different types of products including packaging, building materials, agriculture and medicine. The biodegradable polymers may be synthetic or natural. Additionally, improvements in the mechanical properties of biodegradable polymers are desired to meet more stringent performance requirements, such as stiffness, dimensional stability and modulus.

One potential use for biodegradable polymers having improved properties is for implantable constructs, for example in structural tissue engineering. Presently, autogenous bone (autograft) remains a gold standard in numerous surgeries requiring bone grafting to achieve arthrodesis and fracture union. The inherent osteoinductivity of autograft coupled with its biomechanical strength make it a clear choice for the reconstruction or replacement of load bearing structures in the body. Despite the success of surgical procedures utilizing autograft, complication rates as high as 30% have been associated with the harvest procedure. (Malloy K. M. and Hilibrand, A. S., *Clinical Orthopaedics and Related Research*, 394:27-38, 2002; Samartzis D, Shen F H, Matthews D K, Yoon St, Goldberg E F, An H S, *Spine J.*, 3(6): 451-459. 2003; Wigfield C. C., Nelson R. J., *Spine*, 26:6:687-694, 2001.) These complications include harvest site necrosis and significant post-operative pain and fracture at the harvest site. Arribas-Garcia I, Alcala-Galiano A, Garcia A F, Moreno J J., *Oral Surg Oral Med Oral Pathol Oral Radiol Endod*, 107(6): e12-14, 2009; Hu R. W. and Bohlman H. H., *Clinical Orthopaedics and Related Research*, 309:208-213, 1994.)

Allogenic bone (allograft) has been used in place of autograft. (Samartzis et al., Id., Wigfield et al., Id.) Modern donor screening and sterilization methods have significantly reduced the rates of disease transmission, which until fairly recently was a significant risk in allogenic bone graft procedures. The mechanical properties as well as the osteoinductive capacity of allograft have been shown to be dependent on the type of sterilization employed (Malloy et al., Id; Chau A M, Mobbs R J., *Eur Spine J.*, 18(4): 449-464, 2009.) Additionally, allograft bone is in limited supply in some regions, which can limit its applicability in major surgical procedures, such as scoliosis correction. (Chau et al., Id., Moroni A, Larsson S, Hoang Kim A, Gelsomini L, Giannoudis P V, *J Orthop Trauma*, 23(6): 422-425, 2009.

Given the limitations of autograft and allograft bone, much attention has been given to the development of structural bone graft substitute materials. Ceramic materials, such as the calcium phosphates have been investigated as bone graft substitutes for load bearing applications. (Wigfield et al., Id.) While porous calcium phosphate, such as corraline hydroxyapatite, has high compressive strengths, the brittle nature of the material can lead to progressive collapse of the graft resulting in poor bone healing. (Chau et al., Id.) Porous metallic constructs, such as Trabecular Metal™ (Tantalum, Zimmer Inc., Warsaw Ind.) and Tritanium™ (commercially pure Titanium, Stryker Orthopaedics, Mawah N.J.) have also been introduced as structural bone graft substitutes. The load bearing capacities of porous metal constructs are well documented in both static and dynamic conditions. Unfortunately, long-term implantation of non-resorbing implants is associated with an omni-present risk of infection. Further, the presence of a porous metallic construct may severely limit surgical options if a revision procedure is necessary.

Due to such limitations in the currently available materials, there has been significant interest in developing biodegradable or resorbable polymers for structural bone graft substitute applications. (Chau et al., Id.; Moroni et al., Id.) Numerous methods have been employed to impart a porous structure to resorbable polymers in the hopes of encouraging bone growth. These methods include thermal/pressure induced phase separation, particulate leaching and gas foaming. (Baker K C, Bellair R J, Manitiu M, Herkowitz H N, Kannan R H, *J Mech Behav Biomed Mater.*, 2(6): 620-626, 2009; Georgiou, G., Mathieu, L., Pioletti, D. P., Bourban P.-E., Manson, J.-A. E., Knowles, J. C., and Nazhat, S. N., *J. Biomed Mater Res Part B: Appl Biomater.* 80B: 322-331, 2007; Hu Y, et al., *J Biomed Mater Res.* 59: 563-572, 2001; Mathieu, L. M., Montjovent, M.-O., Bourban, P-E., Pioletti, D. P. and Manson, J.-A. E., *J. Biomed Mater Res.*, 75A:89-97, 2005; Nam Y S, Park T G., *J Biomed Mat Res*, 47: 8-17, 1999.) Phase separation techniques often involve the use of volatile organic solvents which can be detrimental to cell growth. (Nam et al., Id.; Teng X, et al., *J Biomed Mater Res B: Applied Biomaterials*, 81B: 185-193, 2007.) Particulate leaching must be used in combination with other methods, such as phase separation to yield a construct with connected porosity. Gas foaming techniques, such as supercritical carbon dioxide ($scCO_2$), avoid the use of harmful solvents and may not require additional methods to impart an interconnected porous structure. (Baker et al., Id.; Georgiou et al., Id.; Hu et al., Id.; Gualandi C, White L J, Chen L, Gross R A, Shakesheff K M, Howdle S M, Scandola M, *Acta Biomater*, 6(1): 130-136, 2010.)

The mechanical properties of porous resorbable constructs synthesized by the aforementioned means are not suitable for load bearing applications as the compressive modulus and compressive strengths are much lower than that of native bone. Failure of the constructs to withstand physiologic loading conditions may result in a reduced rate of healing and in some conditions may necessitate a revision surgical procedure. Researchers have examined reinforcing the polymer constructs with calcium phosphates (hydroxyapatite, β-TCP), phosphate glass and carbon nanotubes. (Georgiou et al., Id.; Mathieu et al., Id.; Kim S S, Ahn K M, Park M S, Lee J H, Choi C Y, Kim B S, *J Biomed Mater Res A*, 80(1): 206-215, 2007; Khan Y, Yaszemski M J, Mikos A G, Laurencin C T, *Bone Joint Surg Am*, 9-: 36-42, 2008; Rezwan K, Chen Q Z, Blaker J J, Boccacini A R, *Biomaterials*, 27(18): 3413-3431, 2006; Wang Y, et al., *J Biomed Mater Res A*, 86(1): 244-252, 2008.) The addition of these materials to polymer matrices has resulted in modest gains in compressive strength and modulus. Calcium phosphates and phosphate glass particles have a tendency to agglomerate within polymer mixtures, which results in local heterogeneity that is detrimental to mechanical strength. (Georgiou et al., Id.)

Recently, organically modified montmorillonite clays have been investigated as potential reinforcing agents in polymeric matrices. (Horsch, S., Gulari, E. and Kannan, R. J., *Polymer*, 47:7485-7496, 2006; Manitiu M, Bellair R J, Horsch S, Gulari E, Kannan R M., *Macromolecules*, 41(21): 8038-8046, 2008, Pavlidou S, Papspyrides C D, *Prog Poly Sci*, 33: 1119-1198, 2008; Ray S S, Okamoto M, *Prog Poly Sci*, 23: 1524-1543, 2003; Zeng C, et al., *Adv Mater*, 15(20): 1743-1747, 2003.) The clays particles are composed of silicate platelets which are approximately 100-5000 nm in length and 1 nm thick. Platelets are held together by van der Waals forces and the equilibrium platelet spacing of 1 nm is generally modified by chemical techniques. One method of increasing platelet spacing is modification of the clay surface with alkylammonium salts. Increasing the spacing of the clay platelets increases the potential for intimate contact between polymer chains and numerous clay platelets, thus reducing polymer chain mobility and improving mechanical properties. (Horsch et al., Id.; Manitiu et al., Id.; Pavilidou et al., Id.; Ray et al., Id.) The processing method used to create clay-polymer nanocomposites also plays a role in the resulting mechanical behavior. Melt processing, high shear mixing and post-processing heat treatments have been employed to enhance polymer chain-clay platelet contact, with moderate property improvements. (Pavilidou et al., Id.; Ray et al., Id.) Researchers have also used $scCO_2$ processing to improve mechanical properties of polymer-clay nanocomposites. (Horsch et al., Id.; Manitiu et al., Id.; Zeng et al., Id.) Diffusion of $CO_2$ within the clay particles and rapid depressurization leads to an increase in platelet spacing, as well as polymer chain contact. (Horsch et al., Id.; Manitiu et al., Id.)

There is therefore a need to develop a biodegradable polymer nanocomposite system and synthesis route which results in porous constructs with a substantially uniform dispersion of reinforcing particles. In addition, there is a need for biodegradable porous nanocomposites suitable for load-bearing applications and for implantation that may be resorbed over time.

BRIEF SUMMARY

In one aspect of the present invention, a biodegradable nanocomposite is provided. In one aspect, the biodegradable nanocomoposite includes a biodegradable polymer and a reinforcing agent substantially dispersed throughout the biodegradable polymer by rapid depressurization of a supercritical fluid. The biodegradable nanocomposite further includes a plurality of pores formed in the nanocomposite, the plurality of pores having an average pore size greater than about 100 µm.

In another aspect of the present invention, a method of forming a biodegradable nanocomposite is provided. The method includes mixing a biodegradable polymer with a reinforcing agent to form a mixture, contacting the mixture with a supercritical fluid. The method also includes pressurizing and heating the mixture and the supercritical fluid, and catastrophically depressurizing the supercritical fluid to substantially disperse the reinforcing agent within the biodegradable polymer to form the biodegradable nanocomposite.

Advantages of the present invention will become more apparent to those skilled in the art from the following description of the preferred embodiments of the present invention that have been shown and described by way of illustration. As will be realized, the invention is capable of other and different embodiments, and its details are capable of modification in various respects. Accordingly, the drawings and description are to be regarded as illustrative in nature and not as restrictive.

DETAILED DESCRIPTION

Figure 1:
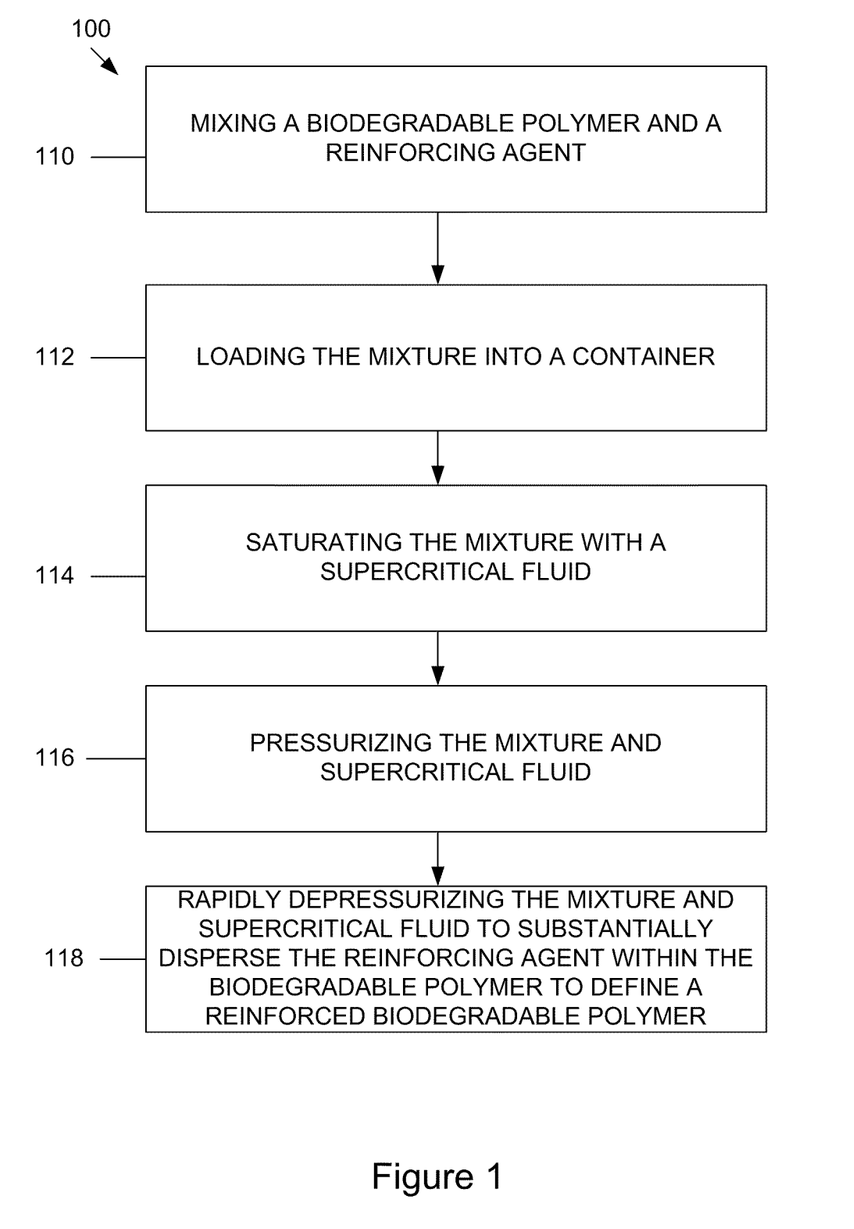
FIG. 1 is a flow chart depicting an embodiment of a method of preparing a biodegradable nanocomposite.

The present invention is directed to a biodegradable nanocomposite and a method of making a biodegradable nanocomposite. The biodegradable nanocomposite includes a biodegradable polymer and a reinforcing agent that are mixed and processed with a supercritical fluid. An embodiment of a method 100 of making the biodegradable nanocomposite is illustrated in FIG. 1. The method includes mixing a biodegradable polymer and a reinforcing agent at 110. The method further includes loading the mixture into a container and saturating the mixture with a supercritical fluid at 112, 114. The method also includes pressurizing the mixture and the supercritical fluid at 116 followed by rapidly depressurizing the mixture and the supercritical fluid to substantially disperse the reinforcing agent within the biodegradable polymer to define a reinforced biodegradable polymer at 118.

The term "biodegradable" is used herein to refer to materials selected to dissipate upon implantation within a body or exposure to the environment, independent of which mechanisms by which dissipation can occur, such as dissolution, degradation, absorption and excretion. The terms "bioabsorbable," "resorbable" or "biodegradable" are used synonymously herein, unless otherwise specified, to refer to the ability of the material or its degradation products to be removed by biological events, such as by fluid transport away from the site of implantation or by cellular activity (e.g., phagocytosis or microbial degradation).

By way of non-limiting example, suitable biodegradable polymers include polymers based on polylactide (PLA), polyglycolide (PGA), poly(lactic-co-glycolic acid (PLGA) polycaprolactone (PCL), their copolymers and mixtures thereof. Additional materials include, but are not limited to, chitosan, methyl cellulose, carboxy-methyl cellulose, poly vinyl acetate, alginate, polyethylene glycol (PEG), poly(2-hydroxyethyl methacrylate) (PHEMA), polymethyl methacrylate (PMMA), ethylene-vinyl acetate (EVA), polyacrylamide, and polyamine.

As is known, if a substance is heated and is maintained above its critical temperature, it becomes impossible to liquefy it with pressure. When pressure is applied to this system, a single phase forms that exhibits unique physicochemical properties. This single phase is termed a supercritical fluid and is characterized by a critical temperature and critical pressure. Supercritical fluids have offered favorable means to achieve solvating properties, which have gas and liquid characteristics without actually changing chemical structure. By proper control of pressure and temperature, a significant range of physicochemical properties (density, diffusivity, dielectric constants, viscosity) can be accessed without passing through a phase boundary, e.g., changing from gas to liquid form.

As is known, a near critical fluid may have a parameter such as a pressure or a temperature slightly below the pressure or the temperature of its critical condition. For example, the critical pressure of carbon dioxide is 73.8 bar and its critical temperature is 301K. At the given temperature, carbon dioxide may have a near critical pressure of between about 3.0 bar and 73.7 bar. At a given pressure, carbon dioxide may have a near critical temperature of between 100K and 300K. A fluid at its near critical condition typically experiences properties such as enhanced compressibility and low surface tension to name a few.

The substantially supercritical fluid of the present invention is preferably a supercritical fluid. The supercritical fluid is preferably carbon dioxide which may exist as a fluid having properties of both a liquid and a gas when above its critical temperature and critical pressure. Carbon dioxide at its supercritical conditions has both a gaseous property, being able to penetrate through many materials and a liquid property, being able to dissolve materials into their components. Although the supercritical fluid is preferably carbon dioxide, the supercritical fluid may comprise other suitable fluids such as methane, ethane, nitrogen, argon, nitrous oxide, alkyl alcohols, ethylene propylene, propane, pentane, benzene, pyridine, water, ethyl alcohol, methyl alcohol, ammonia, sulfur hexaflouride, hexafluoroethane, fluoroform, chlorotrifluoromethane, or mixtures thereof.

It is understood that the substantially supercritical fluid is preferably a supercritical fluid. However, a near-critical fluid may be used in lieu of the supercritical fluid which is referred to hereafter.

By way of non-limiting example, the reinforcing agent used in the present invention is typically an organically modified clay, such as a smectite clay. A smectite clay is a natural or synthetic clay mineral selected from the group consisting of hectorite, montmorillonite, bentonite, beidelite, saponite, stevensite and mixtures thereof. A preferred choice for the smectite clay is montmorillonite. In some embodiments, the smectite clay includes organic modifiers based on ammonium salts. Examples of suitable reinforcing agents include but are not limited to, CLOISITE 93A, CLOISITE 30B, CLOISITE $Na^{++}$, CLOISITE 10A, CLOISITE 11B, CLOISITE 15A, CLOISITE 20A, CLOISITE $Ca^{++}$ (available from Southern Clay Products, Gonzalez, Tex.) and NANOMER I30P (available from Nanocor, Inc. Hoffman Estates, Ill.). Other reinforcing agents include, but are not limited to calcium phosphates and other inorganic materials. The calcium phosphates by way of non limiting example include hydroxyapatite (HA), octacalcium phoshphate (OCP), biomimetic apatite, fluorapatite, beta-tricalciuim phosphate (Beta-TCP), dicalcium phosphate dihydrate (DCPD). The inorganic materials include, but are not limited to carbon nanotubes, single or multi-walled, bioglass, grapheme and calcium carbonate.

The method shown in FIG. 1 may be completed with the use of a number of apparatus known in the art, such as a mixer, extruder, injection molding machine, or any other suitable apparatus capable of loading material such as clay, polymer and supercritical fluid, and capable of maintaining a constant pressure onto the loaded material. The source of supercritical fluid may be any conventional fluid source such as a gas cylinder containing the fluid of choice. In some embodiments, the bioabsorbable polymer may be ground to an average particle size of about 250-500 µm and mixed with the reinforcing agent. The reinforcing agent may be added in an amount from about 0.1 to about 50 weight %, 0.5 to 10 weight %, 0.5 to 5 weight % and preferably from about 1 to 2.5 weight %, by way of non-limiting example.

In some embodiments, for example in structural bone graft substitute applications, the mixed biodegradable polymer and reinforcing agent may be placed in an elongate tube to allow for vertical expansion but not radial expansion of supercritical fluid processed nanocomposites. The elongate tubes may be placed in a supercritical fluid reactor and saturated with the supercritical fluid. Internal pressure within the chamber of the supercritical fluid reactor may be increased. In some embodiments, when carbon dioxide is used at the supercritical fluid, the pressure may be increased to about 10.3 MPa and above, preferably to about 13.8 MPa. The temperature is also increased within the chamber. In some embodiments, the temperature may be increased to about 35° C. and above, preferably to about 100° C. However, other ranges may be used for carbon dioxide and other supercritical fluids without falling beyond the scope or spirit of the present invention. Pressurizing and heating the mixture with the supercritical fluid may be accomplished by any conventional means. In some embodiments, the pressurized and heated incubation may be from about 10 minutes to about 24 hours, depending on the $CO_2$-philicity of the polymer and the reinforcing agent. Incubations on the shorter range of the time range are preferred if polymer and/or therapeutic agents are incorporated within the polymer. An exemplary incubation time is between about 30 minutes and 2 hours, and in some embodiments about 60 minutes.

The method further includes catastrophically or immediately depressurizing the contacted mixture to exfoliate clay particles such that the particles are substantially dispersed, to define a clay-polymer mixture. The step of depressurizing includes immediately depressurizing the mixture down to ambient conditions.

The nanocomposite may be prepared for use in several applications. For example, the nanocomposite may be suitable for structural bone graft substitute applications. In order for the nanocomposite to be useful as a bone graft substitute, the nanocomposite should provide sufficient load bearing capacity and an osteoconductive environment so that the blood supply to the site is sufficient to nourish the graft. The osteoconductive environment is provided by a nanocomposite having a porous structure and interconnected porosity. The nanocomposite should also provide an osteoinductive environment that induces bone formation by recruitment and differentiation of pluripotent cells. The nanocomposite should also provide a resorbable matrix that is replaced by the host bone.

Figure 2:
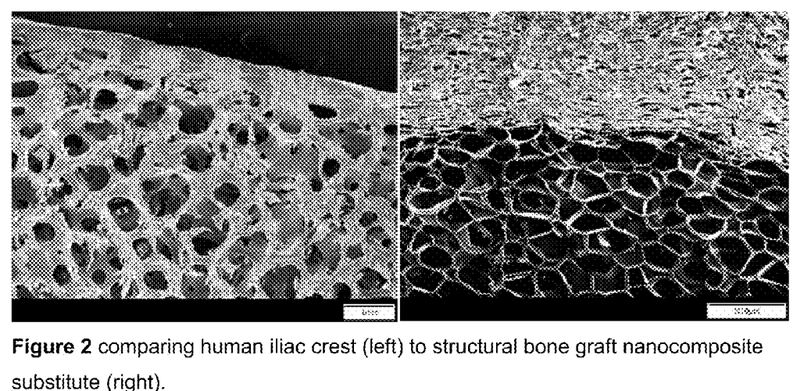
FIG. 2 is an SEM micrograph comparison of human iliac crest (left) to structural bone graft nanocomposite substitute (right)

In the structural bone graft substitutes, the pore size of the nanocomposite graft is important for the reseeding and regrowth of the bone. In some embodiments, the average pore size of the nanocomposite may be about 100-750 µm, and preferably about 150-300 µm, and more preferably about 200-250 µm. In some embodiments, the nanocomposite may include two or more different pore sizes or interconnective porosities. For example, by providing smaller pores or more densely packed pores on the exterior of the nanocomposite to resemble bone formations such as the iliac crest as shown in FIG. 2. The density changes may be provided in the nanocomposite by varying the mold heat transfer characteristics around the outside edge of the nanocomposite, for example. The nanocomposite may be formed so that the compressive strength and the modulus of a construct are similar to the anatomic location into which the nanocomposite is being implanted. For example, for a vertebral body nanocomposite implant, may be formed having a compressive strength of about 3.5-5.0 MPa. The load range for the nanocomposite implant may be about 300N to about 1500N.

The nanocomposites may be delivered to a target site directly by surgical implantation, by injection into the site or by using a natural orifice to access an implantation site or by any method known to one skilled in the art. Delivery sites for structural bone graft nanocomposites include but are not limited to ethmoid, frontal, nasal, occipital, parietal, temporal, mandible, maxilla, zygomatic, incus, stapes, malleus, cervical vertebrae, thoracic vertebrae, lumbar vertebrae, sacrum, sternum, ribs, clavicle, scapula, humerus, ulna, radius, carpal and metacarpal bones, phalanges, ileum, ischium, pubis, pelvis, femur, patella, tibia, fibula, calcaneus, talus, and metatarsal bones.

Nanocomposites may also be delivered to a non-bone site, for example to a tumor, an intraperitoneal space or other soft tissue location. Nanocomposites delivered to non-bone sites may be used to deliver substances to the tissues over time as the nanocomposite resorbs. For example, these nanocomposites may be provided for time-release of chemotherapeutic agents or bioactive agents and the like.

Examples of types of injuries amenable to nanocomposite repair include, but are not limited to, surgical injury, infection, malignancy, or developmental malformation. Nanocomposites may be used for orthopaedic, neurosurgical, cosmetic, and oral and maxillofacial surgical procedures such as the repair of simple and compound fractures and non-unions, external and internal fixations, joint reconstructions, repairs of the vertebral column including spinal fusion and internal fixation, tumor surgery (replacing removed tissue), discectomy, laminectomy, excision of spinal cord tumors, anterior cervical and thoracic operations, repair of spinal injuries, scoliosis, lordosis and kyphosis treatments, intermaxillary fixation of fractures, mentoplasty, temporomandibular joint replacement, alveolar ridge augmentation and reconstruction, inlay bone grafts, implant placement and revision, sinus lifts and similar procedures.

The nanocomposites may be implanted directly or after in vitro culture with cells grown on the nanocomposites. The nanocomposites may also be implanted with a matrix coated on the nanocomposite, such as an extracellular matrix. By way of non-limiting example, the cells provided with the nanocomposites may be bone derived or bone generating cells such as chondrocytes, osteoblasts, osteoclasts, fibroblasts, bone marrow cells, mesenchymal stem cells and/or genetically modified cells or mixtures thereof. The genetically modified cells can be used to deliver biologically active agents for example, wound healing factors or bone formation factors. In some embodiments, the patient's own cells, for example bone marrow or blood enriched for stem cell populations, may be cultured on nanocomposites to expedite graft healing. Other populations of progenitor cells such as mesenchymal stem cells, hematopoietic stem cells and embryonic stem cells or mixtures thereof may also be used.

The nanocomposites may be used to deliver a bioactive agent to the implant site. Bioactive agents include cells as discussed above and further include antibiotics, antivirals, anti-neoplastic agents, anti-inflammatory agents, bioactive agents, growth factors, hematopoietic factors, nutrients and similar agents. Mixtures of bioactive agents may also be included. Non-limiting examples of bone influencing growth factors include bone morphogenic proteins (i.e. BMP's 1-7), bone morphogenic-like proteins (i.e. GFD-5, GFD-7 and GFD-8), epidermal growth factor (EGF), fibroblast growth factor (i.e. FGF 1-9), platelet derived growth factor (PDGF), insulin like growth factor (IGF-I and IGF-II), transforming growth factors (i.e. TGF-β I-III), vascular endothelial growth factor (VEGF), or small molecules that affect the up-regulation of specific growth factors. Bioactive agents may also include agents release other agents that deliver bioactive agents. By way of non-limiting example, microspheres, dendrimers, liposomes and the like may be incorporated into the nanocomposites to release bioactive agents.

Example 1

Effect of $scCO_2$ Processing Parameters on Pure Polymer Construct Architecture

Constructs were synthesized from 100% poly-D-lactic acid (100PDLA), 85:15 poly-D-lactide-co-glycolide (85:15 PDLGA) and 65:35 poly-D-lactide-co-glycolide (65:35 PDLGA) (Lakeshore Biomaterials, Birmingham, Ala.).

Pure polymer constructs were synthesized using 100PDLA, 85:15 PDLGA and 65:35 PDLGA. Briefly, polymers were ground to an average particle size of 250-500 μm and placed in a glass vial (28 mm O.D.×61 mm H) to restrict radial expansion and allow for vertical expansion. 2.0 g of ground polymer was placed in a 20 ml vial, placed into a supercritical fluid reactor and saturated with $CO_2$. The internal pressure was elevated to 10.3, 13.8, or 27.6 MPa at an internal temperature of 35° C. or 100° C. to induce a supercritical phase transformation in the $CO_2$. After 20 minutes of soaking, the reactor was rapidly depressurized at a rate of 0.3-0.4 MPa/s. The samples were removed from the vials and subjected to scanning electron microscopy (SEM, JEOL JSM 6400, JEOL Ltd.).

Processing temperature was found to influence the pore size of the $scCO_2$ processed pure polymer constructs as shown in Table 1. Samples processed at 35° C. exhibited mean pore sizes of 238.0 μm (+/−4.83 μm), with a few pores as large as 400 μm. Pore walls were 32.23 μm (+/−2.47 μm) thick on average. In contrast, the samples processed at 100° C. had pore sizes that averaged 21.5 μm (+/−1.53 μm), pore wall thickness that averaged 17.03 μm (+/−2.33 μm) and a very low extent of pore interconnectivity.

Construct architecture was found to be nearly identical for pure polymer samples processed at 10.3, 13.8 and 26.7 MPa. Pure polymer samples processed at a temperature of 100° C. showed an order of magnitude decrease in pore size, in comparison with samples processed at 35° C., regardless of pressure.

TABLE 1

Pore diameter and pore wall thicknesses of pure polymer constructs as a function of temperature.

| SAMPLE | AVERAGE PORE DIAMETER (μM) | AVERAGE PORE WALL THICKNESS (μM) |
|---|---|---|
| 100 PDLA | | |
| 35° C.-13.8 MPa | 236.2 +/− 4.8 | 32.1 +/− 1.1 |
| 100° C.-13.8 MPa | 22.3 +/− 1.3 | 17.4 +/− 3.5 |
| 85:15 PDLGA | | |
| 35° C.-13.8 MPa | 238.6 +/− 6.5 | 33.0 +/− 4.2 |
| 100° C.-13.8 MPa | 22.1 +/− 2.1 | 16.8 +/− 1.2 |

TABLE 1-continued

Pore diameter and pore wall thicknesses of pure polymer constructs as a function of temperature.

| SAMPLE | AVERAGE PORE DIAMETER (µM) | AVERAGE PORE WALL THICKNESS (µM) |
|---|---|---|
| 65:35 PDLGA | | |
| 35° C.-13.8 MPa | 239.3 +/− 3.2 | 31.6 +/− 2.1 |
| 100° C.-13.8 MPa | 20.1 +/− 1.2 | 16.9 +/− 2.3 |

Example 2

Effect of scCO$_2$ Processing Parameters on Clay-Polymer Nanocomposite Construct Architecture Nanocomposites were formed by adding nanostructured Montmorillonite clay particles (nano-clays). Organic modifiers based on ammonium salts were used to increase the intergallery spacing between silicate platelets, thus facilitating dispersion. The nano-clay used in this study was organically modified with a methyl dehydrogenated tallow (Cloisite 93A, Southern Clay Products, Gonzalez, Tex.). The formula of the methyl dehydrogenated tallow in Cloisite 93A nano-clay is shown below. The nano-clay was used "as-received" from the manufacturer.

where HT is Hydrogenated Tallow (~65% C18; ~30% C16; ~5% C14).

Pure polymer constructs were synthesized using 100PDLA as described in Example 1 above. Briefly, polymers were ground to an average particle size of 250-500 µm and placed in an elongate container (28 mm O.D.×61 mm H). The polymer-filled containers, each with 2.0 g of ground polymer, were placed into a supercritical fluid reactor and saturated with CO$_2$. The internal pressure was elevated to 13.8 MPa at an internal temperature of 35° C. to induce a supercritical phase transformation in the CO$_2$. After 60 minutes of soaking, the reactor was rapidly depressurized at a rate of 0.3-0.4 MPa/s.

Clay-polymer nanocomposite constructs were synthesized using 100PDLA and CLOISITE 93A. 2.0 g of ground 100PDLA polymer with total clay loading of 2.5 wt % were mixed and ground to an average particle size of 250-500 µm. Ground nanocomposite particles were placed in elongate containers (28 mm O.D.×61 mm H) and placed into the supercritical fluid reactor and saturated with CO$_2$. The internal pressure of the reactor was elevated to 13.8 MPa and the temperature was raised to either 35° C. or 100° C. After 60 minutes of soaking in the supercritical CO$_2$, the reactor was rapidly depressurized at a rate of 0.3-0.4 MPa/s.

Figure 3A:
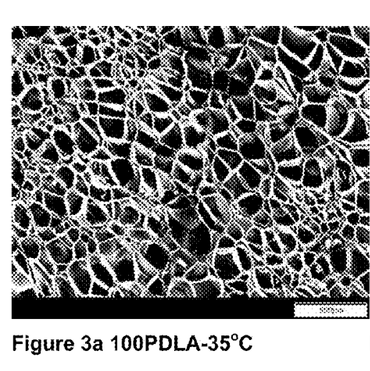
FIGS. 3a-3c are SEM micrographs illustrating the effect of the temperature on $scCO_2$ processing of composites including clay-polymer mixtures.
Figure 3B:
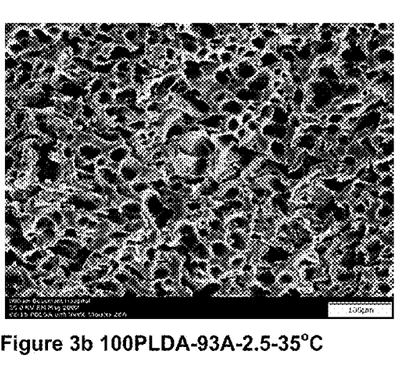
Figure 3C:
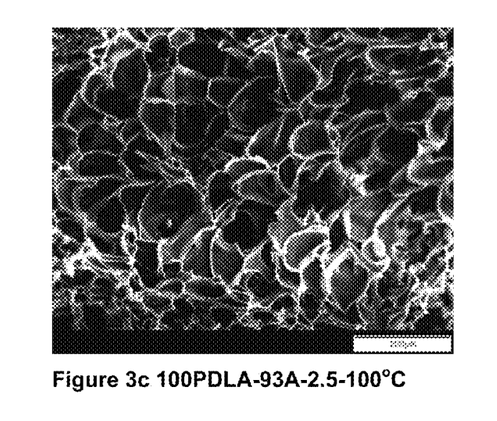

As shown in FIGS. 3a-3c, the addition of the clay to the construct dramatically reduces the pore size in the clay-polymer nanocomposite construct in comparison to the pure polymer construct when the constructs are processed at 35° C. (FIG. 3b.) Surprisingly, elevating the processing temperature of the clay-polymer nanocomposite construct to 100° C. results in increased pore size suitable. (FIG. 3c.) See Table 2 below showing a comparison of the average pore size of the clay-polymer nanocomposite constructs processed at 100° C. compared to the pure polymer constructs processed at 35° C. to obtain similar pore sizes.

Example 3

Synthesis of Biodegradable Polymer Nanocomposites for Further Evaluation

Pure polymer constructs were synthesized using 100PDLA. Briefly, polymers were ground to an average particle size of 250-500 µm and placed in a steel tube (28 mm O.D.×61 mm H). The tube restricts radial expansion of the polymer, but allows for expansion in the vertical direction (confined). The polymer-filled tubes, each with 2.0 g of ground polymer, were placed into a supercritical fluid reactor and saturated with CO$_2$. The internal pressure was elevated to 13.8 MPa at an internal temperature of 35° C. to induce a supercritical phase transformation in the CO$_2$. After 60 minutes of soaking, the reactor was rapidly depressurized at a rate of 0.3-0.4 MPa/s.

Clay-polymer nanocomposite constructs were synthesized using 100PDLA and CLOISITE 93A. 2.0 g of ground 100PDLA polymer with total clay loading of 1 wt %, or 2.5 wt % were mixed and ground to an average particle size of 250-500 µm. Ground nanocomposite particles were placed in steel tubes (28 mm O.D.×61 mm H) and placed into the supercritical fluid reactor and saturated with CO$_2$. The internal pressure of the reactor was elevated to 13.8 MPa and the temperature was raised to 100° C. After 60 minutes of soaking in the supercritical CO$_2$, the reactor was rapidly depressurized at a rate of 0.3-0.4 MPa/s. The process was repeated to yield samples of 100PDLA with 1 wt % Cloisite 93A (100PDLA-93A-1) and 2.5 wt % 93A (100PDLA-93A-2.5).

Example 2

SEM Analysis of Biodegradable Polymer Nanocomposites

100PDLA, 100PDLA-93A-1 and 100PDLA-93A-2.5 constructs were freeze-fractured with liquid nitrogen in the vertical (direction of CO$_2$ escape) and transverse (direction perpendicular to CO$_2$ escape) directions. Fracture surfaces were coated with a thin film of AuPd and subjected to scanning electron microscopy. SEM was performed at a working distance of 15 mm and an accelerating voltage of 20 kV. Measurements of pore size, pore wall thickness and qualitative assessments of pore interconnectivity were performed using digital image analysis software (Revolution, 4Pi Analysis). Measurements were conducted on a minimum of three vertical and three transverse fracture surfaces. At least eight images were captured from each fracture surface. Pore dimensions were measured for 20 pores per fracture surface image.

Figure 4:
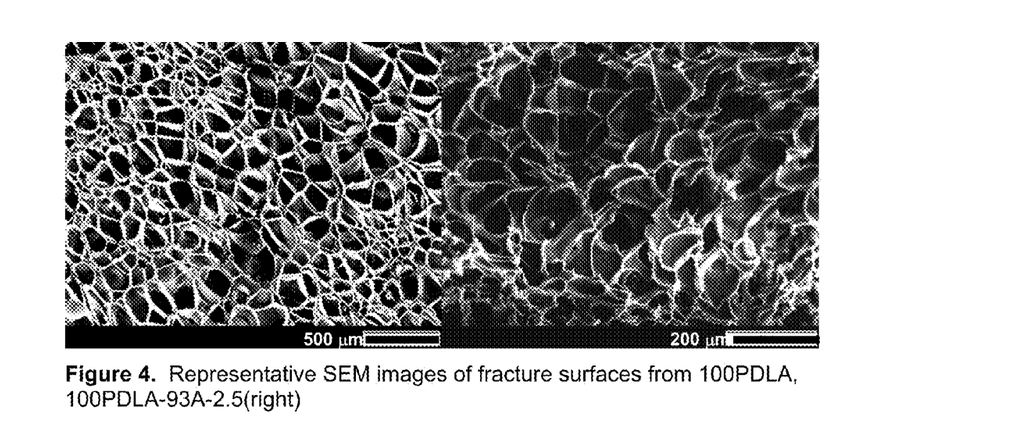
FIG. 4 is an SEM micrograph comparison of pure polymer pores (left) and clay-polymer nanocomposite pores (right).

Results of the SEM measurements are shown in Table 1 below. 100PDLA pure polymer constructs had mean pore diameters of 236.2 µm (+/−4.8 µm), respectively. Similar pore diameters were noted for nanocomposite constructs, 100PDLA-93A-1 and 100PDLA-93A-2.5 as illustrated in FIG. 4 and shown in Table 2. No differences in pore interconnectivity were observed as assessed by analysis of fracture surfaces by SEM.

TABLE 2

Pore diameter and pore wall thicknesses of pure polymer and nanocomposite constructs.

| SAMPLE | CLAY | MEAN PORE DIAMETER (μM) | MEAN PORE WALL THICKNESS (μM) |
|---|---|---|---|
| 100 PDLA | None | 236.2 +/− 4.8 | 32.1 +/− 1.1 |
| 100 PDLA-93A-1 | 1 wt % | 243.1 +/− 10.1 | 27.0 +/− 3.6 |
| 100 PDLA-93A-2.5 | 2.5 wt % | 239.8 +/− 13.3 | 29.8 +/− 5.3 |

Example 3

Characterization of Dispersion in Biodegradable Polymer Nanocomposites

A Rigaku SmartLab Diffractometer with a Cu Kα X-ray source (λ=1.54 Å) and an accelerating voltage of 40 kV at a current of 40 mA was used to determine the intergallery spacing of the clay/polymer nanocomposites. Samples were placed in a custom made, zero-background quartz sample holder that is 0.9 mm in depth and diffraction scans were collected from 0.1 to 10° 2θ at a scan rate of 3.0 degrees/min at a step size of 0.3 degrees. Several scans were obtained from different locations in the sample and verified to be reproducible when diffraction patterns were superimposed on one another. The 2θ angle was determined using the JADE software that accompanies the diffractometer and the $d_{001}$ spacing for the clays was calculated using Braggs' Law of diffraction. The intergallery spacing was then found by subtracting 1 nm (platelet thickness) from the $d_{001}$ spacing.

Figure 5:
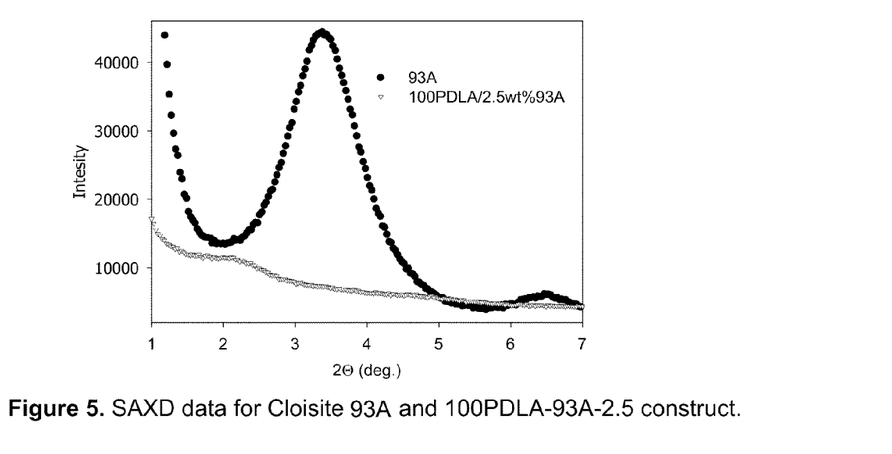
FIG. 5 illustrates a comparison of the small angle x-ray diffraction spectra.

The diffraction spectrum of the 100PDLA-93A-2.5 nanocomposite showed a shift in the 001 peak of pure Cloisite 93A from 3.36° to 4.41° 2θ, as shown in FIG. 5. Using the Bragg equation it was determined that this magnitude of shift in the 2θ position corresponds to an increase in platelet spacing of 1.79 nm (from 2.62 nm to 4.41 nm) after $scCO_2$ processing. Increased platelet spacing, as determined by X-ray diffraction has been used to determine the degree of intercalation of organically modified clays in polymer matrices.

Example 4

Rheology Measurements of the Biodegradable Polymer Nanocomposites

A Rheometric Scientific RSA II rheometer (shear sandwich geometry 15.98 mm×12.7 mm×0.55 mm) was used to perform melt rheological measurements under oscillatory shear. Samples were prepared by melt pressing the polymer and nanocomposite constructs into a mold at 80° C. between Teflon plates followed by annealing under vacuum at 80° C. to remove any residual carbon dioxide. The materials were loaded and allowed to equilibrate for 1 hour at the desired temperature. Rheological measurements were performed at 80° C. and 120° C. for all samples. Strain sweeps were performed to ensure that the dynamic moduli were linear in the strain range used and the linear viscoelastic measurements were made at low strains ($\gamma_o$<0.05) to minimize microstructure destruction. The frequency range used was 0.01=ω=100 rad/s and the property of time-temperature superposition was used to create master curves with a reference temperature of 80° C.

Figure 6:
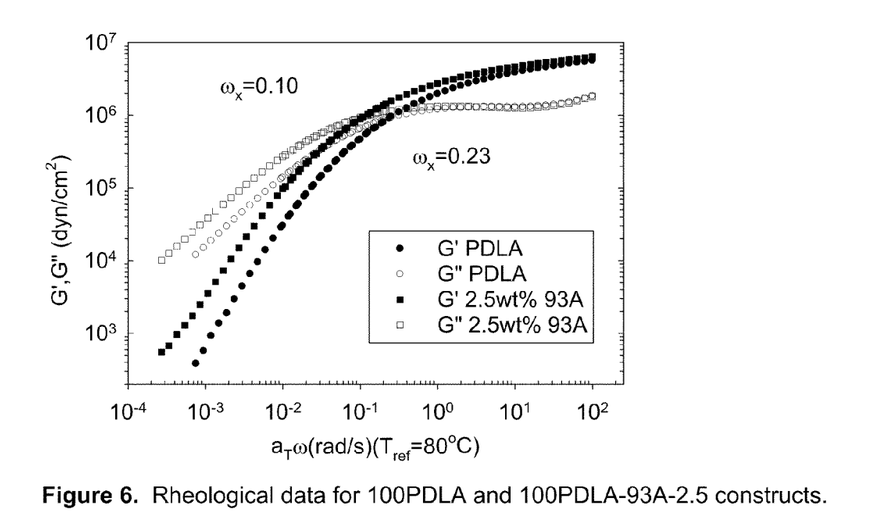
FIG. 6 illustrates rheological data for 100PDLA and 100PDLA-93A-2.5 constructs.

As shown in FIG. 6, a shift in the crossover frequency, characteristic of the polymer chain relaxation time, from 0.23 to 0.10 rad/s was observed as well as a decrease in the slope of the elastic modulus in the terminal regime of the 100PLDA-93A-2.5 nanocomposite. Characterization of the rheological behavior of the pure and nanocomposite constructs showed that the nano-clay reduced the mobility of polymer chains within the construct. A shift in the frequency at which the storage (G') and loss (G") moduli cross indicates a change in the so-called "characteristic relaxation time" of the polymer. In this case, a reduction in the crossover frequency from 0.23 rad/s to 0.10 rad/s is indicative of over a doubling of the relaxation time of the polymer. Additionally, the low frequency "terminal" region of the storage modulus has a reduced slope when compared to the pure polymer which indicates that there is a significant amount of clay dispersion in the processed construct. Such strong polymer clay interactions and dispersion are necessary for the efficient transfer of stress from the matrix to the filler that is necessary to enhance mechanic properties.

Example 5

Mechanical Testing of the Biodegradable Polymer Nanocomposites

Cylindrical cores with a diameter of 10 mm were obtained from constructs by using an osteochondral biopsy system. The cores were sectioned to a height of 10 mm and trimmed with a scalpel to ensure that the ends were parallel. The samples were placed between smooth stainless steel platens in a servohydraulic materials testing machine (850 Mini-Bionix, MTS Inc., Eden Prairie, Minn.). Constructs were loaded in compression under displacement control at a rate of 0.5 mm/min until a strain of 50% was reached.

The compressive strength of the constructs was defined as the maximum load divided by the initial cross sectional area. Compressive modulus was determined by calculating the slope of the linear region of the load-displacement curve. A student t-test was used to determine the statistical significance of mechanical data as a function of construct composition.

Figure 7:
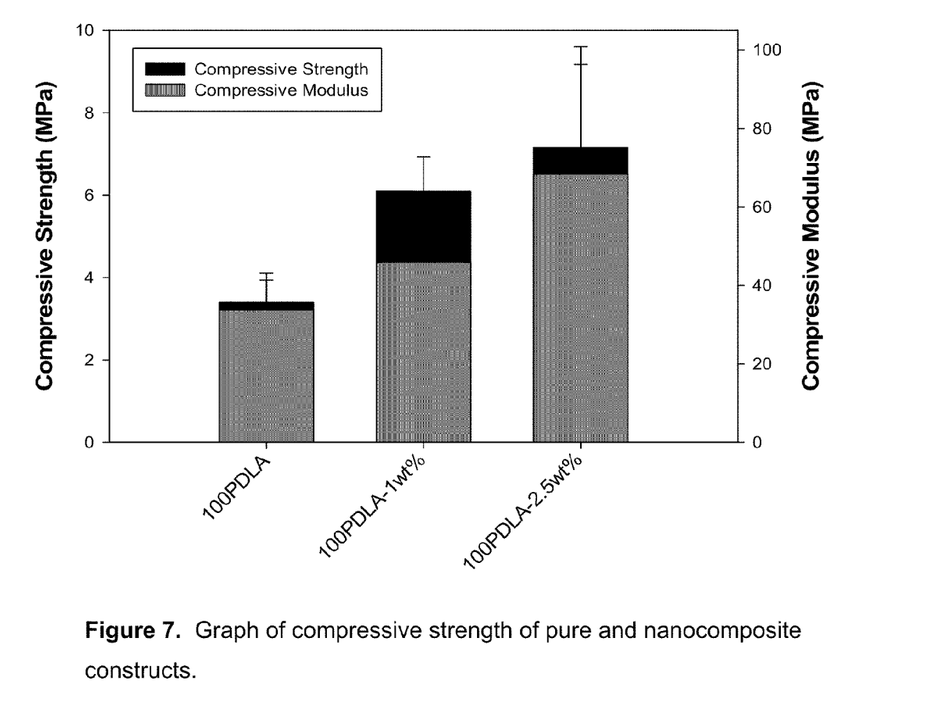
FIG. 7 is a graph showing compressive strength of pure polymer and nanocomposite constructs.

As shown in FIG. 7, pure polymer constructs (100PDLA) exhibited a compressive strength of 3.41 MPa (+/−0.54 MPa) and a compressive modulus of 33.79 MPa (+/−9.30 MPa). The addition of 1 wt % Cloisite 93A nano-clay particles to the 100PDLA increased the compressive strength to 6.10 MPa (+/−0.83 MPa) and compressive modulus to 45.92 MPa (+/−15.33 MPa). Nanocomposite constructs containing 2.5 wt % Cloisite 93A nano-clay showed an average compressive strength of 7.15 MPa (+/−2.02 MPa) and average compressive modulus of 68.42 MPa (+/−32.41 MPa).

Example 6

Biocompatibility Testing of the Biodegradable Polymer Nanocomposites

Pre-osteoblastic cells from mouse calvaria (MC3T3-E1, ATCC, Manassas, Va.) were cultured in α-modified minimum essential medium containing 2 mM L-glutamine and 1 mM sodium pyruvate (α-MEM, Gibco, USA). The medium was supplemented with 10% fetal bovine serum (ATCC, Manassas, Va.), 100 U/ml penicillin, and 100 μg/ml streptomycin (Sigma, St. Louis, Mo.). Cell cultures were maintained in 5% $CO_2$ with 95% air at 37° C. until 85% confluence. Cells were lifted using 0.05% trypsin/0.5 mM EDTA solution (Sigma), concentrated, resuspended in medium, and counted using a hemocytometer.

Cells were seeded directly onto nanocomposite constructs at a density of $1 \times 10^6$ cells per construct. Controls were performed using the same cell density on polystyrene culture plates. Cells were allowed to attach to constructs for 1 hour before the addition of differentiation medium consisting of standard growth medium supplemented with 10 mM β-glycerophosphate and 0.2 mM ascorbic acid 2-phosphate (Sigma). After six days in culture, 50 nM melatonin was added to the differentiation medium. Cultures were maintained for 21 days and medium changed every 48 hours.

Alkaline phosphatase (ALP) activity of the differentiated cells was determined at 21 days by colorimetric assay (QuantiChrom ALP Assay Kit, BioAssay Systems, Hayward, Calif.). Constructs were washed with phosphate buffered saline (PBS, Sigma) and incubated for 30 minutes in lysis buffer containing 1% Triton X-100 in PBS. The lysates were used to determine ALP activity. A one way analysis of variance was used to compare the ALP activities of cells cultured on the two nanocomposites and the polystyrene culture plates.

Seeded nanocomposite constructs were also subjected to SEM to examine cell morphology and mineralization. Constructs were fixed in gluteraldehyde for 24 hours and then subjected to critical point drying. After drying, the samples were sputter-coated with AuPd and visualized with SEM at a working distance of 8 mm and an accelerating voltage of 20 kV. Energy dispersive X-ray spectroscopy (EDX, Link Analytical) was used to characterize the composition of regions of suspected mineralization.

Figure 8:
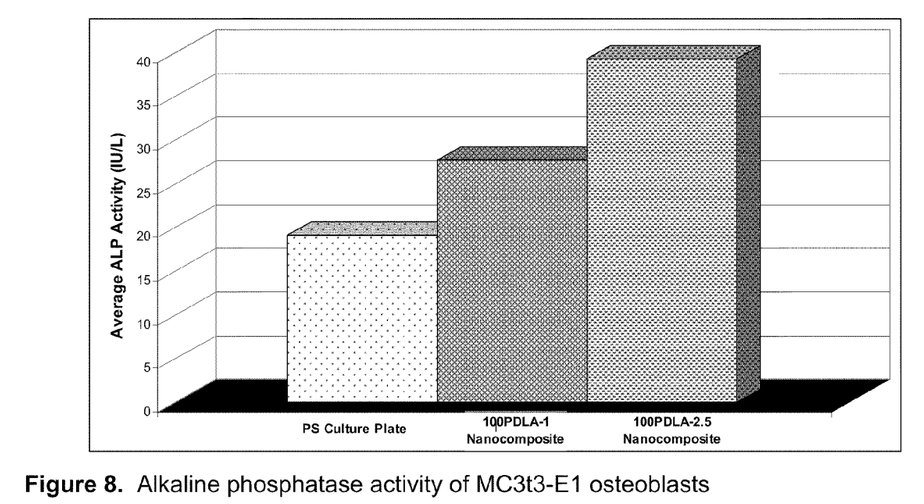
FIG. 8 is a graph of alkaline phosphatase activity.

The state of differentiation of pre-osteoblasts seeded on polystyrene culture plates and the 100PLDA-93A-1 and 100PDLA-93A-2.5 nanocomposite constructs was assayed at 21 days by measuring the production of alkaline phosphatase. Both nanocomposite constructs yielded higher output of alkaline phosphatase activity when compared to the polystyrene culture plates as shown in FIG. 8. The difference in ALP activity between the culture plate and the 100PDLA-93A-1 was not statistically significant (p=0.128). There was also not a statistically significant difference in ALP activity between the 100PDLA-93A-1 and 100PDLA-93A-2.5 nanocomposite constructs (p=0.062). However, the difference in ALP activity between the 100PDLA-93A-2.5 nanocomposites and polystyrene culture plates was statistically significant (p=0.002).

Examination of the nanocomposite scaffolds after culturing cells for 21 days using SEM revealed copious amounts of extracellular matrix deposition on both the 100PDLA-93A-1 and 100PDLA-93A-2.5 nanocomposite constructs. The deposits were comprised mainly of calcium and phosphorus as determined by EDX. This composition is indicative of the mineralization process. Cells and calcium phosphate deposits could be seen within pores deep in the porous network of the constructs. The presence of cells and deposits in the center of the constructs indicates that cells are able to infiltrate the open porous structure of the nanocomposite constructs. Some surface degradation was noted on the outermost pore walls on both nanocomposite formulations. This degradation manifested as irregularly shaped pores The porous morphology of the biodegradable polymer nanocomposites indicates suitability for use as a scaffold for bone growth. Both pure and nanocomposite constructs synthesized for this study exhibited average pore diameters of 236.2 μm, 243.1 μm and 239.8 μm for 100PDLA, 100PDLA-93A-1 and 100PDLA-93A-2.5 constructs, respectively. Pore interconnectivity is also essential for the in vivo success of scaffolds, as it ensures the ability to transport nutrients to the center of the constructs.

Although the invention herein has been described in connection with a preferred embodiment thereof, it will be appreciated by those skilled in the art that additions, modifications, substitutions, and deletions not specifically described may be made without departing from the spirit and scope of the invention as defined in the appended claims. It is therefore intended that the foregoing detailed description be regarded as illustrative rather than limiting, and that it be understood that it is the following claims, including all equivalents, that are intended to define the spirit and scope of this invention.

The invention claimed is:

1. A biodegradable nanocomposite comprising:
 a biodegradable polymer;
 a reinforcing agent comprising a clay substantially dispersed throughout the biodegradable polymer by rapid depressurization of a supercritical fluid, the clay having an increased platelet spacing after dispersion throughout the biodegradable polymer by rapid depressurization of the supercritical fluid relative to the clay prior to the supercritical fluid treatment; and
 a plurality of pores formed in the nanocomposite, the plurality of pores having an average pore size greater than about 100 μm; wherein the nanocomposite comprises a compressive strength of about 6.10 MPa or greater.

2. The biodegradable nanocomposite of claim 1, wherein the average pore size is about 150-300 μm.

3. The biodegradable nanocomposite of claim 1, wherein the polymer is selected from polylactide (PLA), polyglycolide (PGA), poly(lactic-co-glycolic acid (PLGA), polycaprolactone (PCL), chitosan, methyl cellulose, carboxy-methyl cellulose, poly vinyl acetate, alginate, polyethylene glycol (PEG), poly(2-hydroxyethyl methacrylate) (PHEMA), polymethyl methacrylate (PMMA), ethylene-vinyl acetate (EVA), polyacrylamide, and polyamine, their copolymers and mixtures thereof.

4. The biodegradable nanocomposite of claim 1, wherein the polymer comprises a synthetic or biologic polymer swellable in carbon dioxide.

5. The biodegradable nanocomposite of claim 1, wherein the reinforcing agent is physically or chemically modified to enhance interaction with the biodegradable polymer.

6. The biodegradable nanocomposite of claim 1, wherein the supercritical fluid is carbon dioxide.

7. The biodegradable nanocomposite of claim 1, wherein the nanocomposite comprises a bone graft substitute.

8. The biodegradable nanocomposite of claim 1, wherein the nanocomposite further comprises a bioactive agent.

9. The biodegradable nanocomposite of claim 8, wherein the bioactive agent comprises progenitor cells, antibiotics, antivirals, anti-neoplastic agents, growth factors, microspheres, dendrimers, liposomes and mixtures thereof.

10. The biodegradable nanocomposite of claim 1, wherein the nanocomposite comprises a compressive strength of about 7.15 MPa or greater.

11. A method of forming a biodegradable nanocomposite, the method comprising:
 mixing a biodegradable polymer with a reinforcing agent comprising a clay to form a mixture;
 contacting the mixture with a supercritical fluid;
 pressurizing and heating the mixture and supercritical fluid;
 catastrophically depressurizing the supercritical fluid to substantially disperse the clay within the biodegradable polymer so that the clay has an increased platelet spacing after dispersion throughout the biodegradable polymer by rapid depressurization of the supercritical fluid relative to the clay prior to the supercritical fluid treatment to form the biodegradable nanocomposite comprising a plurality of pores formed in the nanocomposite, the plurality of pores having an average pore size greater than about 100 μm; wherein the nanocomposite comprises a compressive strength of about 6.10 MPa or greater.

12. The method of claim 11, further comprising restricting radial expansion of the mixture.

13. The method of claim 11, comprising heating the mixture to about 35° C. or greater.

14. The method of claim 11, comprising elevating the pressure to above about 10.3 MPa.

15. The method of claim 11, comprising depressurizing the supercritical fluid at a rate of about 0.25-0.5 MPa per second.

16. The method of claim 11, further comprising implanting the nanocomposite to replace at least a portion of a bone.

17. The biodegradable nanocomposite of claim 1, wherein the clay comprises about 2.5 weight percent of the nanocomposite or less.

18. The biodegradable nanocomposite of claim 1, wherein the clay comprises about 2.5 weight percent of the nanocomposite or less.

19. The method of claim 11, further comprising forming the biodegradable nanocomposite including about 2.5 weight percent clay or less.

* * * * *